(12) United States Patent
Chou

(10) Patent No.: US 6,692,756 B2
(45) Date of Patent: *Feb. 17, 2004

(54) ALOE VERA GLOVE AND MANUFACTURING METHOD

(75) Inventor: Belle L Chou, Union City, CA (US)

(73) Assignee: Shen Wei (USA), Inc., Union City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/114,807

(22) Filed: Apr. 2, 2002

(65) Prior Publication Data

US 2002/0110584 A1 Aug. 15, 2002

Related U.S. Application Data

(63) Continuation of application No. 09/898,632, filed on Jul. 3, 2001, now Pat. No. 6,423,328, which is a continuation of application No. 09/288,067, filed on Apr. 7, 1999, now Pat. No. 6,274,154.

(51) Int. Cl.[7] .............................................. A01N 25/34
(52) U.S. Cl. ......................... 424/402; 424/400; 424/443
(58) Field of Search ................................ 424/401, 402, 424/443, 400

(56) References Cited

U.S. PATENT DOCUMENTS

| | | |
|---|---|---|
| 2,916,036 A | 12/1959 | Sutton |
| 3,662,054 A | 5/1972 | Wollmann et al. |
| 4,122,554 A | 10/1978 | Stager |
| 4,185,330 A | 1/1980 | Stager |
| 4,186,445 A | 2/1980 | Stager |
| 4,775,372 A | 10/1988 | Wilberg |
| 5,133,090 A | 7/1992 | Modak et al. |
| 5,417,968 A | 5/1995 | Staats |
| 5,614,202 A | 3/1997 | DeFina |
| 5,679,399 A | 10/1997 | Shlenker et al. |
| 5,682,617 A | 11/1997 | Tumas |
| 5,869,072 A * | 2/1999 | Berry .............................. 2/159 |
| 5,910,567 A * | 6/1999 | Tanaka et al. .......... 264/331.13 |
| 6,117,119 A | 9/2000 | Gould |
| 6,274,154 B1 * | 8/2001 | Chou ............................... 2/158 |
| 6,589,544 B2 | 7/2003 | Leong |
| 2001/0006680 A1 | 7/2001 | Mansouri |

FOREIGN PATENT DOCUMENTS

| | | |
|---|---|---|
| GB | 8704858 | 9/1987 |
| JP | 409002962 | 1/1997 |
| WO | WO 94/12115 | 6/1994 |
| WO | WO 00/59450 | 10/2000 |
| WO | WO 01/39582 A1 | 6/2001 |
| WO | WO 01/67864 A2 | 9/2001 |

OTHER PUBLICATIONS

"Le sōōthe™ Aloe Vera & Vitamin E Latex Glove Examination", 2 page Product Brochure (2002).
"Le sōōthe™ Aloe Vera & Vitamin E Powder Free Latex Exam Glove", 1 page Product Brochure (2002).
Mayo Health Web page, "Your Body's First Line of Defense," 1 page (Jun. 19, 1999).
Mayo Health Web page, "The Anatomy of Your Skin," 1 page (Jun. 19, 1999).
IASC Website, "Aloe Vera: Its Potential Use in Wound Healing and Disease Control in Oral Conditions By Dr. Timothy E. Moore, D.D.S./M.S., P.C.," 2 pages (May 12, 1999).

(List continued on next page.)

Primary Examiner—Thurman K. Page
Assistant Examiner—Robert M. Joynes
(74) Attorney, Agent, or Firm—Intellectual Property Law Group LLP; Otto O. Lee; C. George Yu

(57) ABSTRACT

A moisturizing and therapeutic glove is disclosed which includes a thin layer of Aloe Vera coated evenly and uniformly on an inside surface of the glove. Aloe Vera is attached to the surface through a dehydration process achieved with a controlled drying method. Aloe Vera soothes the hand during the wearing of the glove.

15 Claims, 1 Drawing Sheet

OTHER PUBLICATIONS

Safeskin™ Powder–Free Latex Gloves Product Packaging; Kimberly–Clark Corporation, 2001 (6 pages).

Crosstex® International Aloe Vera Ultra Plus® Powderless Product Packaging for Small Non–Chlorinated Powderless Exam Gloves; about Dec., 2001 (6 pages).

Ultra Preserve with Aloe Vera Packaging for Polytex™ Lined Rubber Latex Examination Gloves; Tillotson Healthcare Corporation (undated) (6 pages).

Packaging for AloeDerm® Textured Powder–Free with Aloe Vera; Top Quality Manufacturing Inc. (undated) (6 pages).

Promotional Letter to Dental Professionals from Quantum re: SoftSkin™ With Aloe Vera (undated) (2 pages).

Informational brochure re: Softskin™ Powder–Free Latex Exam Gloves with Aloe Vera (undated) (2 pages).

Promotional advertisement from Quantum Labs Incorporated re: Softskin™ with Aloe Vera (undated) (1 page).

Packaging for Softskin™ With Aloe Vera Powder Free Latex Exam Gloves; Quantum Labs Incorporated (undated) (2 pages).

Sale of Quantum/Softskin™ as described in the above Softskin™ literature labeled C10–C13 (approx. May 1999) (1 page).

Introductory brochure for Aloetouch™ distributed by Medline Industries, Inc. 2000 (2 pages).

Sale of Aloetouch™ Glove to Medline as described in the above literature labeled C15 (approx. Oct. 1999) (1 page).

* cited by examiner

ALOE VERA GLOVE AND MANUFACTURING METHOD

CROSS-REFERENCE

The present application is a continuation application of commonly-owned U.S. patent application Ser. No. 09/898,632, filed Jul. 3, 2001 now U.S. Pat. No. 6,423,328, which is a continuation application of commonly-owned U.S. patent application Ser. No. 09/288,067 filed on Apr. 7, 1999 (now U.S. Pat. No. 6,274,154), which are both hereby incorporated by reference.

BACKGROUND

This invention relates generally to hand care products, and specifically relates to applying Aloe Vera on the inner surface of disposable gloves to protect and soothe the hands during and after application of disposable gloves.

Disposable gloves are widely used as a protective measure to insulate hands from the objects handled by the wearer of gloves. To allow ease in handling objects, disposable gloves are made of thin and elastic material to minimize the space between the skin and the glove. Due to poor air circulation resulting from tight insulation, hand sweating is a common problem among glove wearers. Prolonged wearing of disposable gloves causes a moist environment on the surface of the hand that allows viruses, bacteria, yeast, and fungus to grow and multiply. Itchiness is a frequent result of wearing disposable examination gloves for extended periods.

Powders are commonly used on the inner surface of gloves to alleviate sweating and to make donning, wearing and removal of gloves easier. However, continuous sweating can easily overwhelm the thin layer of powder that is commonly attached to the surface of the glove. This is especially the case when continuous and frequent wearing of gloves is required. For example, dentists may continuously wear gloves during a dental surgical procedure for up to 40 minutes. In addition, hand washing is necessary after the use of powdered gloves. Frequent hand washing to remove powders may also cause excess dryness of the skin.

The need for disposable gloves that can prevent adverse side effects caused by extensive use is apparent. Various patents disclose different types of gloves that contain lotions. During glove use the lotions come into contact human skin and condition the skins. For example, U.S. Pat. No. 5,614,202 discloses a moisturizing glove that contains a middle layer saturated with lotion. The porous inner layer allows the lotion to pass through and contact the skin. U.S. Pat. Nos. 4,186,445 and 4,185,330 disclose gloves that have inner lining made of a lotion absorbent material. By impregnating the lotion onto the absorbent material, the lotion can condition the hands during application of the gloves.

A common feature of the above disclosures is the use of multiple layers in the glove design. Compared to single layer disposable gloves, the complex design of multiple layer gloves makes production far more costly. Most importantly, the thickness of the layers and the complicated structures of the gloves hinder hand flexibility when the glove wearer tries to pick up and manipulate objects. Such multiple layer designs are suitable for moisturizing hands, but are not suitable for manipulating objects, especially for professions that require handling of fine tasks with precision.

Disposable gloves are generally made of three types of materials: natural rubber latex, acrylonitrile, and polyvinyl chloride. Natural rubber latex is sensitive to oil-based substances. Prolonged contact between latex and oil-based substance can adversely affect durability and flexibility of the latex material. Most commercially available lotions contain oil-based substances. The use of lotions in prior arts will substantially shorten the shelf life of a natural rubber glove.

There is therefore a need for low cost disposable gloves that can apply moisturizing and therapeutic substances to the hands during the glove use without leaving a greasy feel or look to the skin, while at the same time, retain the characteristics and functions of conventional single layer gloves.

SUMMARY

The present invention satisfies these needs. This invention is a novel disposable glove with Aloe Vera uniformly applied to the inner surface of the glove through a dehydration process, and a method for making such a glove.

One object of this invention is to condition and soothe the hands during glove use.

Another object of this invention is to produce a glove that is equivalent to a single layer glove in the user's ability to pick up and manipulate objects.

Still another object of this invention is to prevent growth of bacteria, viruses, yeast and fungi on the hands, which become more active in a wet environment resulting from sweating during prolonged or frequent wearing of gloves.

A related object is to cause the anti-microbial substance to dissociate and release from the glove surface in response to the degree of wetness of hand.

A further object is to preserve the shelf life of glove by using natural non-oil based substance and to preserve the activity of the therapeutic substance by keeping the substance in a dehydrated state.

The above objects are accomplished by applying Aloe Vera evenly to the inner surface of a disposable examination glove through dehydration.

The objects are further accomplished by a method of manufacturing the Aloe Vera glove. The disposable gloves are first treated with chlorine solution to wash off any powders, extract soluble substances in the composite material, and kill microorganisms. After drying, the gloves are turned inside out and dipped into a prepared Aloe Vera solution to saturate the outer surface. The gloves are then dried in a tumbling heater within a controlled narrow range of temperature between 45° C. and 65° C., and for a specific length of time. This causes water to evaporate and the Aloe Vera to evenly coat the glove surface. After cooling to room temperature, the gloves are inverted so that the side with Aloe Vera coating is facing inside.

DRAWINGS

DETAILED DESCRIPTION OF THE INVENTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
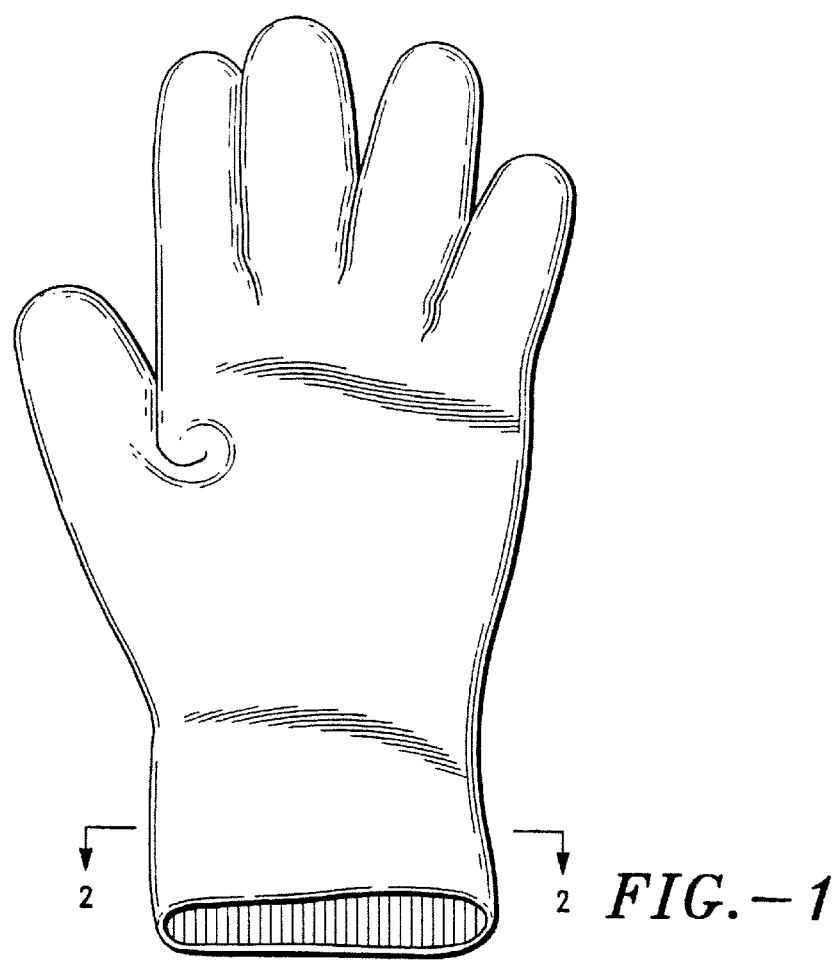
FIG. 1 is the front perspective view of an Aloe Vera glove constructed in accordance with the principles of the present invention.
Figure 2:
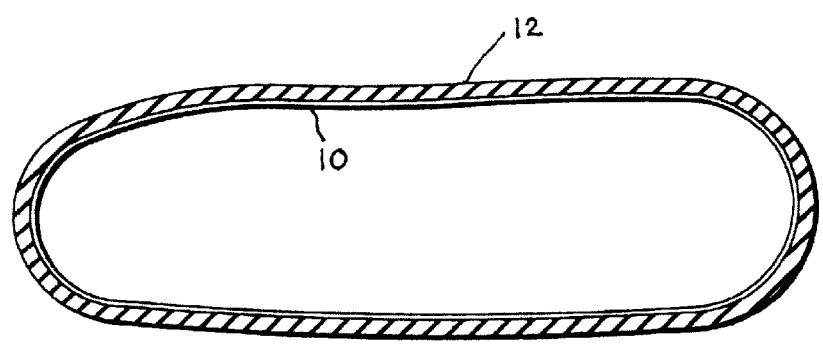
FIG. 2 is a sectional view taken along the lines 2—2 of FIG. 1.

The invention is a disposable glove as illustrated in FIG. 1, which has Aloe Vera 10 evenly coated on the inner surface in a dehydrated state, as illustrated in FIG. 2. The glove retains the features of a disposable examination glove, which is simple and convenient to use and allows the wearer to handle fine tasks with precision. The invention also discloses a manufacturing method for modifying a disposable glove by coating Aloe Vera on the inner surface of the glove. The glove is coated with Aloe Vera 10 through dehydration that is accomplished by a well-controlled heating process.

A disposable glove is made of various materials to form a layer 12. Resinous materials such as vinyl or polymer materials such as acrylonitrile are common choices. Three commonly used materials for making disposable gloves are natural rubber latex, acrylonitrile and polyvinyl chloride.

In one preferred embodiment, the glove is made of natural rubber latex. Since natural rubber latex is sensitive to oil-based substances, gloves made of natural rubber latex should not be exposed to oil-based substances. In this invention, Aloe Vera is used to coat the gloves and it does not contain any detectable oil-based substances. Coating gloves with Aloe Vera does not affect the glove's shelf life. In another preferred embodiment the glove is made of acrylonitrile polymer.

Aloe Vera is a natural plant extract that has a long history of folk medicine usage. Aloe Vera has been used for external treatment of wounds, burns and skin irritations, and internal treatment of various conditions. Aloe Vera is a popular ingredient in skin-care products. It is also a powerful anti-inflammatory and anti-microbial agent. Aloe Vera is soluble in water and contains non-detectable oil content.

Aloe Vera glove retains the characteristic of a disposable glove without any visible modification, and is easy and convenient to use. The affiliation between Aloe Vera and the glove surface is through a force provided by dehydration. Such affiliation is loosened when sweat dissolves Aloe Vera. The longer a glove is worn, the more likely the hand will sweat, and consequently more Aloe Vera will be dissolved and disassociated from the glove surface, and be applied to hand. The active ingredients in Aloe Vera can then condition hand skin and prevent microorganisms from growing under the wet condition.

In one preferred embodiment, 100% Aloe Vera gel is used to coat the gloves. Aloe Vera is evenly and uniformly distributed on the inner surface of the glove at a thickness of about 0.01 millimeter. The association between Aloe Vera and the surface is achieved by a non-covalent force provided through dehydration.

The method of manufacturing gloves involves treating a commercially available disposable glove to eliminate residue powders, soluble substances, and microorganisms, dipping it into an Aloe Vera solution and heating the glove to cause water to evaporate.

A glove is preferably first treated with a chlorine solution or chlorine gas. Chlorine solution can help to sterilize the gloves, to wash off powders, and most importantly for natural latex gloves, to dissolve residual proteins that could potentially trigger severe allergic reactions among repeat users. After the outside surface of the glove is treated with the chlorine solution, and the glove is again treated with the chlorine solution. The residue chlorine is neutralized by using ammonia and the gloves are then dried.

An Aloe Vera solution will then be prepared. One hundred percent concentrated Aloe Vera gel is dissolved in distilled water to generate an Aloe Vera solution. The preferred concentration of the solution is about 20%. To associate Aloe Vera with the surface of the glove, Aloe Vera solution can be sprayed onto the surface of the glove. Alternatively, the glove can be immersed into the Aloe Vera solution. The latter method is preferred because it creates a complete and even distribution of the Aloe Vera solution.

In one preferred embodiment, the dipping process is accomplished by grouping a number of gloves in a batch to achieve higher manufacturing efficiency. The gloves are immersed in the solution for at least 10 minutes to allow adequate absorbency.

Aloe Vera is attached to the surface of the glove through a controlled dehydration process. The water in the Aloe Vera solution is caused to evaporate through heating. Although a higher temperature will cause water to evaporate quicker, excess heat may damage the gloves. For example, gloves exposed to excessive heat of over 70° C. may turn brownish and become brittle. To shorten the heat exposure time, a heating oven is preheated to about 45° C. before the gloves are introduced. The oven has a temperature control mechanism to maintain a maximum temperature. In a preferred embodiment the maximum temperature is set at approximately 65° C. and the heating process lasts from about 35 to 40 minutes. The dehydration process provides an affiliation force so that Aloe Vera can remain associated with the glove surface for an extensive period of time.

Even distribution of Aloe Vera on the glove surface maximizes therapeutic treatment of the hand and minimizes contact between the skin and the glove's composite material. Stationary drying is not preferred because the Aloe Vera solution tends to flow in the direction of the force of gravity. In a preferred embodiment the heating oven has a device to tumble during the heating to make Aloe Vera distribute evenly on the glove surface and to form a uniform coating.

Afterward the gloves are cooled to room temperature. The gloves are then inverted so that the surface with the Aloe Vera faces inside.

What is claimed is:

1. A method of manufacturing a disposable examination glove comprising
   a) forming a disposable glove from a flexible material,
   b) coating the interior surface of said glove with Aloe Vera and a liquid carrier, and
   c) evaporating the liquid carrier from the coating to form a dehydrated coating of Aloe Vera attached to the interior surface of said glove, so that the Aloe Vera contacts the hand of a person wearing said glove.

2. The method of claim 1 wherein said disposable glove is made from a natural rubber latex.

3. The method of claim 2 wherein said coating of Aloe Vera is substantially free of oil-based substances.

4. The method of claim 1 wherein said dehydrated coating is substantially 100% Aloe Vera.

5. The method of claim 1 wherein said glove is made of a single layer of flexible material prior to being coated.

6. The method of claim 1 wherein said liquid carrier is water.

7. The method of claim 1 wherein said coating is formed by dipping said glove into said Aloe Vera and liquid carrier.

8. The method of claim 1 wherein said coating is formed by spraying said glove with a solution of Aloe Vera in said liquid carrier.

9. The method of claim 1 wherein said interior surface of said glove is treated with chlorine prior to coating said surface with Aloe Vera and a liquid carrier.

10. The method of claim 1 wherein said glove is turned inside out prior to coating said interior surface with Aloe Vera and a liquid carrier.

11. The method of claim 10 wherein said glove is turned right side out after evaporating the liquid carrier from the coating to form a dehydrated coating of Aloe Vera attached to said interior surface.

12. A method of manufacturing a disposable examination glove comprising
   a) forming a disposable glove from a single layer of flexible material,
   b) applying an aqueous solution of Aloe Vera to the interior surface of said glove, and
   c) removing the liquid carrier to form a dehydrated coating of Aloe Vera attached to the interior surface of said glove, so that the Aloe Vera contacts the hand of a person wearing said glove.

13. A method of manufacturing a disposable examination glove comprising
   a) forming a disposable glove from a single layer of natural rubber latex,
   b) turning said glove inside out,
   c) applying an aqueous solution of Aloe Vera to the surface of said glove that is normally the inner surface of said glove but is the outer surface while said glove is turned inside out,
   d) removing the liquid carrier to form a dehydrated coating of Aloe Vera attached to the surface of said glove while said glove is still turned inside out, and
   e) turning the glove right side out, so that the dehydrated coating of Aloe Vera contacts the hand of a person wearing said glove.

14. A method of reducing the adverse effects of a disposable examination glove on the skin of a person wearing the glove, comprising coating the interior surface of the glove with a dehydrated coating of Aloe Vera attached to said interior surface.

15. The method of claim 1, wherein the coating step occurs after the forming step.

* * * * *